United States Patent
Chen et al.

(10) Patent No.: US 12,070,213 B2
(45) Date of Patent: Aug. 27, 2024

(54) SURGICAL MEDICAL DEVICES

(71) Applicant: Covidien LP, Mansfield, MA (US)

(72) Inventors: Mingfei Chen, Santa Rosa, CA (US); Rhonda L. Staneart, Santa Rosa, CA (US); Emily E. Jacobs, Durham, CT (US); Gerald N. Hodgkinson, Killingworth, CT (US); Brian C. Graham, Santa Rosa, CA (US); Monideepa Chatterjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/113,811

(22) Filed: Feb. 24, 2023

(65) Prior Publication Data
US 2023/0263525 A1    Aug. 24, 2023

Related U.S. Application Data

(60) Provisional application No. 63/313,302, filed on Feb. 24, 2022.

(51) Int. Cl.
*A61B 17/072* (2006.01)

(52) U.S. Cl.
CPC ............ *A61B 17/07292* (2013.01); *A61B 2017/07257* (2013.01); *A61B 2017/07271* (2013.01)

(58) Field of Classification Search
CPC .......... A61B 17/07292; A61B 17/04; A61B 17/0401; A61B 2017/07257; A61B 2017/07271; A61B 2017/0053; A61B 2017/2825; A61B 2017/2829; A61B 2017/0406

USPC ........................................ 606/148, 151, 154
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

International Search Report and Written Opinion of the International Searching Authority issued in corresponding application PCT/US2023/013790 mailed May 15, 2023 (15 pages).

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

Surgical stapling devices have a surgical buttress attached to an anvil jaw member, a cartridge jaw member, or both. In use, the surgical buttress reinforces a staple line formed upon application of staples from the surgical stapling device and minimizes leaks which may exude from the staple line and/or tissue being stapled by the surgical stapling device.

19 Claims, 6 Drawing Sheets

(56) References Cited

U.S. PATENT DOCUMENTS

| | | |
|---|---|---|
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,319,264 B1 * | 11/2001 | Tormala ............ A61F 2/0063 606/151 |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B1 | 8/2002 | Rehil |
| 6,443,964 B1 | 9/2002 | Ory et al. |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |

(56) References Cited

U.S. PATENT DOCUMENTS

| | | |
|---|---|---|
| 7,021,086 B2 | 4/2006 | Ory et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |

(56) References Cited

U.S. PATENT DOCUMENTS

| | | |
|---|---|---|
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |

(56) References Cited

U.S. PATENT DOCUMENTS

| | | |
|---|---|---|
| 2009/0001122 A1* | 1/2009 | Prommersberger ................ A61B 17/07292 227/176.1 |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0080498 A1* | 4/2012 | Shelton, IV ......... A61B 17/072 227/180.1 |
| 2012/0187179 A1* | 7/2012 | Gleiman ............. A61B 17/072 227/181.1 |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0155916 A1* | 6/2014 | Hodgkinson ......... A61F 2/0063 606/151 |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119389 A1* | 5/2017 | Turner ................. A61B 17/068 |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |
| 2022/0313261 A1* | 10/2022 | Shelton, IV ..... A61B 17/07292 |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2008595 A2 | 12/2008 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 9516221 A1 | 6/1995 |
| WO | 9838923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

* cited by examiner

SURGICAL MEDICAL DEVICES

CROSS-REFERENCE TO RELATED APPLICATIONS

This application claims the benefit of the filing date of provisional U.S. Patent Application No. 63/313,302 filed on Feb. 24, 2022.

TECHNICAL FIELD

The present disclosure relates to surgical devices, such as surgical buttresses, for use with wound closure devices.

BACKGROUND

Surgical stapling instruments are employed by surgeons to sequentially or simultaneously apply one or more rows of fasteners, e.g., staples or two-part fasteners, to body tissue for the purpose of joining segments of body tissue together. Such instruments generally include a pair of jaws or finger-like structures between which the body tissue to be joined is placed. When the stapling instrument is actuated, or "fired," longitudinally moving firing bars contact staple drive members in one of the jaws. The staple drive members push the surgical staples through the body tissue and into an anvil in the opposite jaw, which forms the staples. If tissue is to be removed or separated, a knife blade can be provided in the jaws of the device to cut the tissue between the lines of staples.

When operating on certain tissue, such as lung, esophageal, intestinal, duodenal, and vascular tissue, it is important to effectively seal the tissue which can be particularly prone to air or fluid leakage. Preventing or reducing air or fluid leakage can significantly decrease post operative recovery time.

Improved surgical repair materials, capable of use as surgical buttresses for sealing and/or reinforcing staple lines in tissue, remain desirable.

SUMMARY

The present disclosure relates to medical devices, including surgical stapling devices, which can be used to repair tissue.

In aspects, a surgical stapling device of the present disclosure includes an end effector having an anvil jaw member and a cartridge jaw member pivotally coupled to one another, the anvil jaw member and the cartridge jaw member being relatively movable such that the end effector is movable between an open position and a clamped position. A surgical buttress is attached to the anvil jaw member, the cartridge jaw member, or both.

In some aspects, a surgical stapling device of the present disclosure includes an end effector including an anvil jaw member and a staple cartridge jaw member pivotally coupled to one another, the anvil jaw member and the staple cartridge jaw member being relatively movable such that the end effector is movable between an open position and a clamped position, A surgical buttress may be attached to the anvil jaw member, the staple cartridge jaw member, or both, the surgical buttress including a substrate and a porous layer.

In some aspects, in use, the substrate of the surgical buttress is adjacent tissue, and the porous and/or swellable layer of the surgical buttress is adjacent the substrate of the surgical buttress.

In other aspects, in use, the porous and/or swellable layer of the surgical buttress is adjacent tissue, and the substrate of the surgical buttress is adjacent the porous and/or swellable layer of the surgical buttress.

In yet other aspects, in use, a first porous and/or swellable layer of the surgical buttress is adjacent tissue, the substrate of the surgical buttress is adjacent the first porous and/or swellable layer of the surgical buttress, and a second porous and/or swellable layer of the surgical buttress is adjacent the substrate of the surgical buttress.

In aspects, the surgical buttress further comprises a non-permeable layer.

In some aspects, in use, the substrate of the surgical buttress is adjacent tissue, the porous and/or swellable layer of the surgical buttress is adjacent the substrate of the surgical buttress, and the non-permeable layer of the surgical buttress is adjacent the porous and/or swellable layer of the surgical buttress.

In other aspects, in use, the porous and/or swellable layer of the surgical buttress is adjacent tissue, the substrate of the surgical buttress is adjacent the porous and/or swellable layer of the surgical buttress, and the non-permeable layer of the surgical buttress is adjacent the substrate of the surgical buttress.

In aspects, the substrate of the surgical buttress has pores in an amount from about 65% to about 90% of the volume of the substrate, and a thickness from about 0.05 mm to about 0.5 mm, in embodiments from about 0.1 mm to about 0.2 mm.

In some aspects, the porous and/or swellable layer of the surgical buttress has pores in an amount from about 65% to about 99% of the volume of the porous layer, and a non-compressed thickness from about 100 µm to about 2000 µm.

In other aspects, the non-permeable layer of the surgical buttress has a thickness from about 5 µm to about 50 µm.

In other aspects, a surgical stapling device of the present disclosure includes an end effector including an anvil jaw member and a staple cartridge jaw member pivotally coupled to one another, the anvil jaw member and the staple cartridge jaw member being relatively movable such that the end effector is movable between an open position and a clamped position. The surgical stapling device also includes a surgical buttress attached to the anvil jaw member, the staple cartridge jaw member, or both, the surgical buttress including a substrate, a porous layer, and a non-permeable layer.

In aspects, the present disclosure also provides a method for treating tissue, which includes stapling tissue with the recited surgical stapling device.

In aspects, a surgical buttress of the present disclosure includes a substrate having pores in an amount from about 65% to about 85% of the volume of the substrate, and a thickness from about 0.05 mm to about 0.5 mm; a porous and/or swellable layer having pores in an amount from about 65% to about 99% of the volume of the porous layer, and a non-compressed thickness from about 100 µm to about 2000 µm; and a non-permeable layer having a thickness from about 5 µm to about 50 µm.

In some aspects, in use, the substrate of the surgical buttress is adjacent tissue, the porous and/or swellable layer of the substrate is adjacent the substrate of the surgical buttress, and the non-permeable layer of the surgical buttress is adjacent the porous and/or swellable layer of the surgical buttress.

BRIEF DESCRIPTION OF THE DRAWINGS

Aspects of the presently disclosed surgical stapling apparatus are described herein with reference to the drawings wherein.

DETAILED DESCRIPTION

Figure 1:
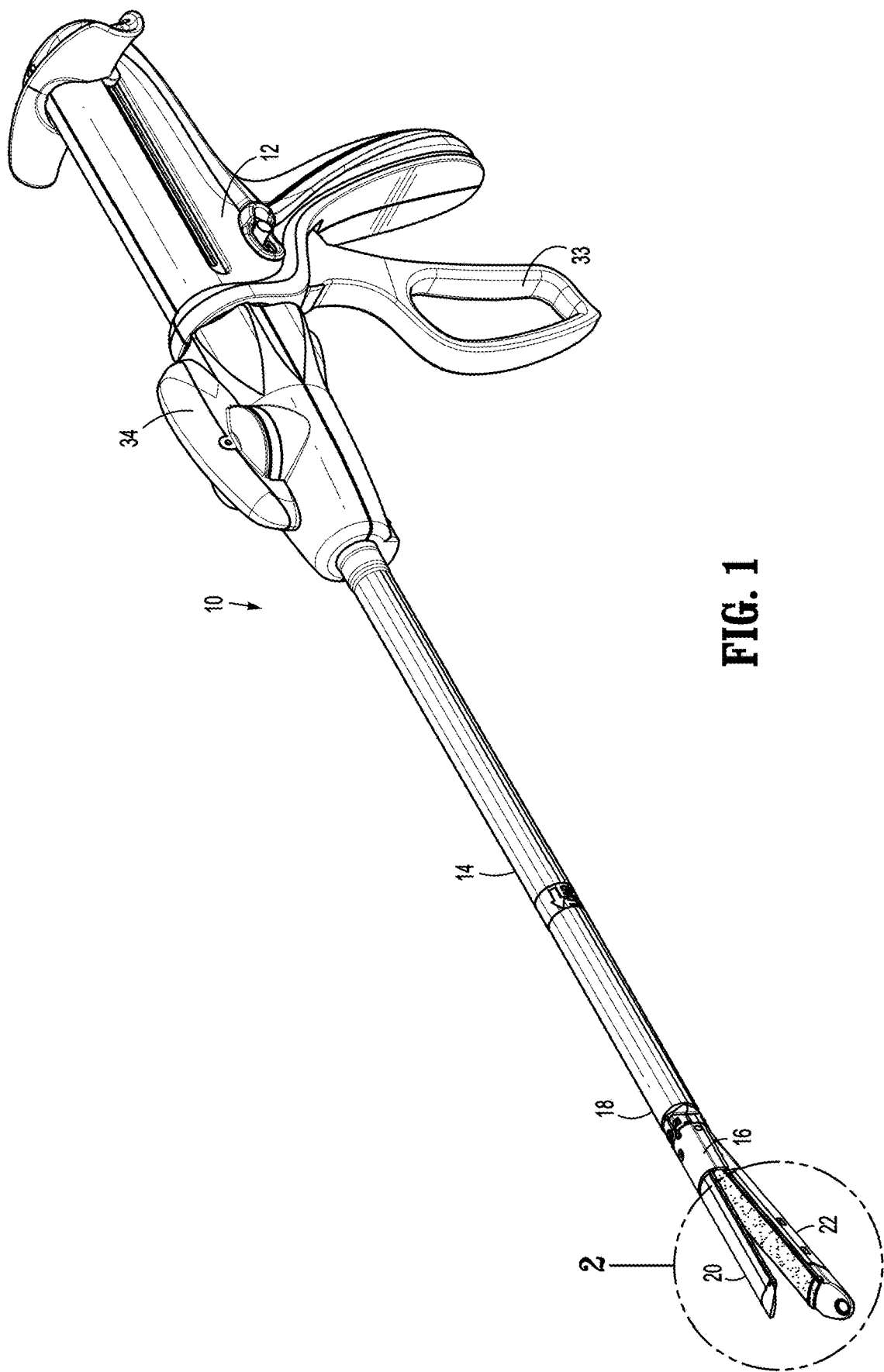
FIG. 1 is a perspective view of a surgical stapling apparatus including a handle housing, an adapter assembly, an end effector, and surgical buttresses attached to components thereof in accordance with an aspect of the present disclosure.

Various exemplary aspects of the present disclosure are discussed herein below in terms of surgical buttresses for use with tissue fixation devices, in aspects surgical staples. While the below disclosure discusses in detail the use of these surgical buttresses with staples, it will be appreciated that surgical stapling apparatuses of the present disclosure include a range of surgical buttressing materials and film-based materials that may be used to mechanically support tissues, reinforce tissues along staple or suture lines, and decrease the incidence of fluid leakage and/or bleeding of tissues. For example, other suitable materials which may be used with the surgical stapling apparatus of the present disclosure include hernia patches and/or tissue scaffolds.

The surgical buttress used with a surgical stapling apparatus of the present disclosure is in the form of a generally rectangular body having a distal end and a proximal end, with opposing lateral sides that run along the length of the elongate rectangular body portion from the distal end to the proximal end.

In aspects, a surgical buttress of the present disclosure may be formed of multiple layers. The layers may include a substrate, a porous and/or swellable layer, a non-permeable layer, and any combination thereof. In some aspects, the substrate may be a non-woven substrate. As used herein, a "porous layer" encompasses a layer that is porous and/or swellable, as further disclosed and/or described herein.

It should be understood that a variety of surgical stapling apparatuses may be utilized with a surgical buttress of the present disclosure. In aspects, linear staplers may be utilized such as, for example, those including EndoGIA™ Reinforced Reload with Tri-Staple Technology™ and other staplers with Tri-Staple™ technology, available through Medtronic, (North Haven, CT), as well as other anastomosis staplers, such as, for example, EEA™, CEEA™, GIA™, EndoGIA™, and TA™, also available through Medtronic. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire disclosure of which is incorporated by reference herein); laparoscopic staplers (see, e.g., commonly owned U.S. Pat. Nos. 6,330,965 and 6,241,139, each entitled "Surgical Stapling Apparatus," the entire disclosures of each of which are incorporated by reference herein); and transverse anastomosis staplers (see, e.g., commonly owned U.S. Pat. Nos. 5,964,394 and 7,334,717, each entitled "Surgical Fastener Applying Apparatus", the entire disclosures of each of which are incorporated by reference herein).

Aspects of the presently disclosed surgical buttress and surgical stapling apparatus will now be described in detail with reference to the figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Referring now to FIG. 1, there is disclosed an exemplary surgical stapling apparatus or surgical stapler 10 for use in stapling tissue and applying a surgical buttress to tissue. The surgical stapling apparatus 10 generally includes a handle 12 having an elongate tubular member 14 extending distally from the handle 12. An end effector 16 is mounted on a distal end 18 of the elongate tubular member 14. The end effector 16 includes an anvil assembly including a staple clinching anvil jaw member 20 and a cartridge assembly including a staple cartridge jaw member 22 configured to receive a staple cartridge 32. The end effector 16 may be permanently affixed to the elongate tubular member 14 or may be detachable and thus replaceable with a new end effector 16. The staple clinching anvil jaw member 20 is movably mounted on the distal end 18 of the end effector 16 and is movable between an open position spaced apart from the staple cartridge jaw member 22 to a closed position substantially adjacent the staple cartridge jaw member 22.

The surgical stapling apparatus 10 further includes a trigger 33, as seen in FIG. 1, movably mounted on the handle 12. Actuation of the trigger 33 initially operates to move the anvil jaw member 20 from the open to the closed position relative to the staple cartridge jaw member 22 and subsequently actuates the surgical stapling apparatus 10 to apply lines of staples to tissue. In order to properly orient the end effector 16 relative to the tissue to be stapled, the surgical stapling apparatus 10 is additionally provided with a rotation knob 34 mounted on the handle 12. Rotation of the rotation knob 34 relative to the handle 12 rotates the elongate tubular member 14 and the end effector 16 relative to the handle 12 so as to properly orient the end effector 16 relative to the tissue to be stapled.

Reference may be made to commonly owned U.S. Pat. Nos. 5,915,616, 6,330,965, and 6,241,139, the disclosures of each of which are incorporated by reference herein, for a detailed discussion of the construction and operation of the surgical stapling apparatus 10.

Figure 2:
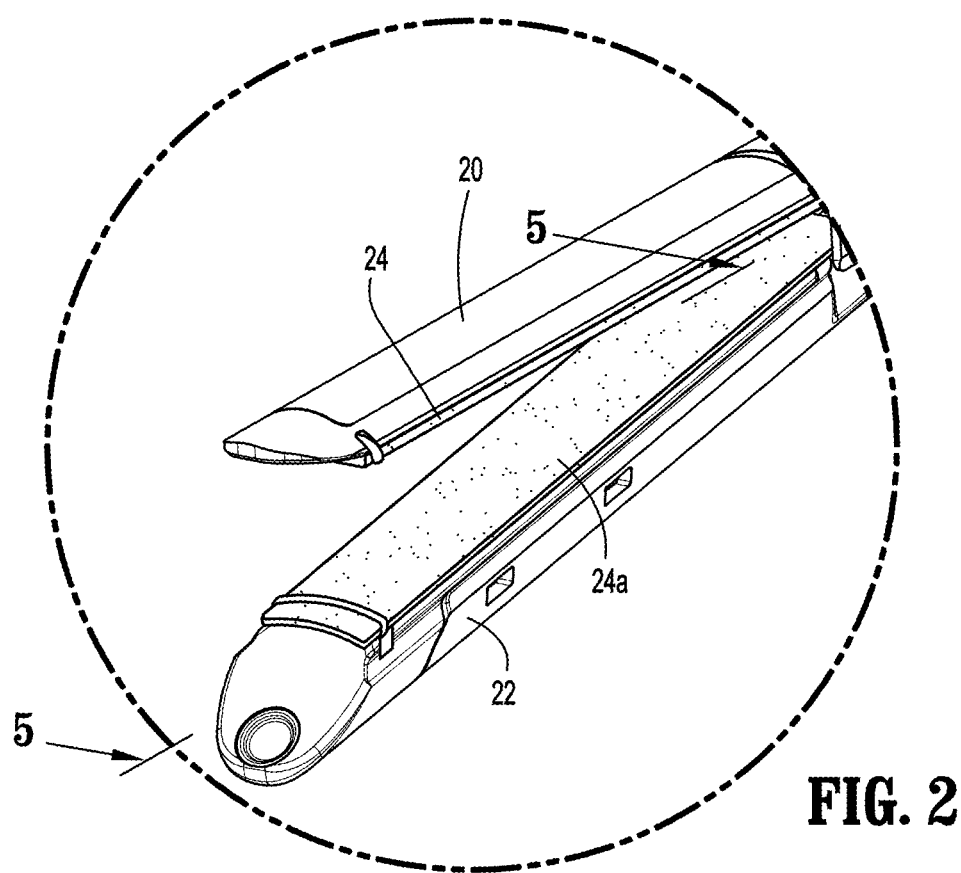
FIG. 2 is an enlarged view of the indicated area of detail shown in FIG. 1.
Figure 3:
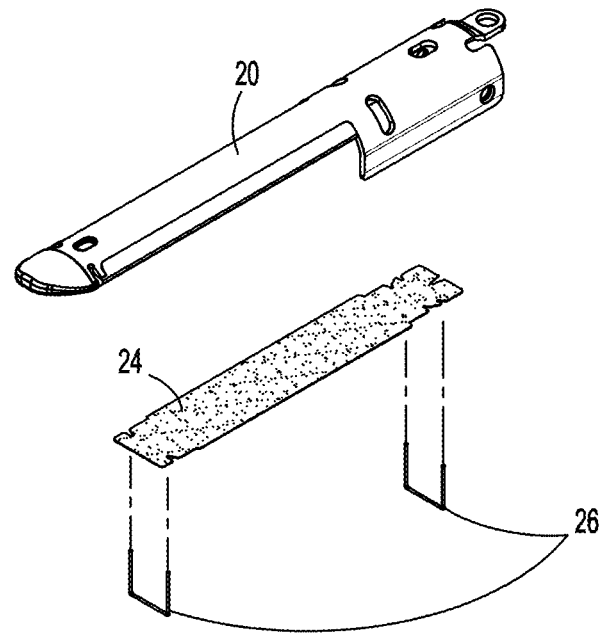
FIG. 3 is a perspective view of an anvil assembly of the end effector of the surgical stapling apparatus shown in FIG. 1, showing how a surgical buttress in accordance with an aspect of the present disclosure may be attached thereto.
Figure 4:
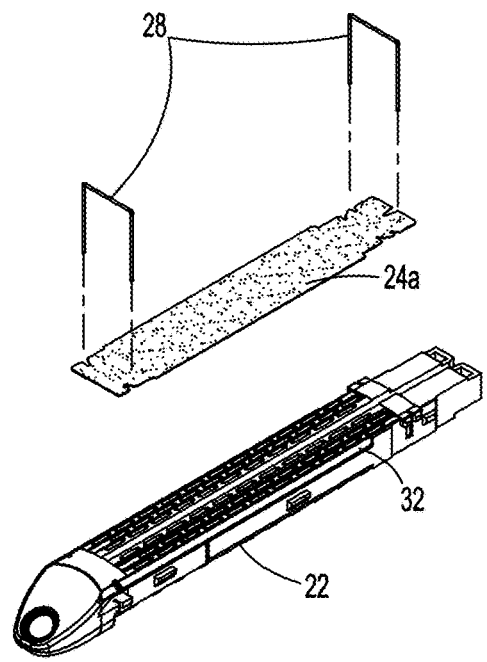
FIG. 4 is a perspective view of a cartridge assembly of the end effector of the surgical stapling apparatus shown in FIG. 1, showing how a surgical buttress in accordance with an aspect of the present disclosure may be attached thereto.

Referring to FIGS. 2-4, the staple clinching anvil jaw member 20 and the staple cartridge jaw member 22 may be provided with surgical buttresses 24, 24a. The surgical buttresses 24, 24a are provided to reinforce and seal staple lines applied to tissue by the surgical stapling apparatus 10. The surgical buttresses 24, 24a may be configured in any shape, size, or dimension suitable to fit any surgical stapling, fastening, or firing apparatus.

As illustrated in FIG. 3, the surgical buttress 24 may be attached to the staple clinching anvil jaw member 20 with sutures 26. Similarly, as illustrated in FIG. 4, the surgical buttress 24a may be attached to the staple cartridge jaw member 22 with sutures 28.

Figure 5:
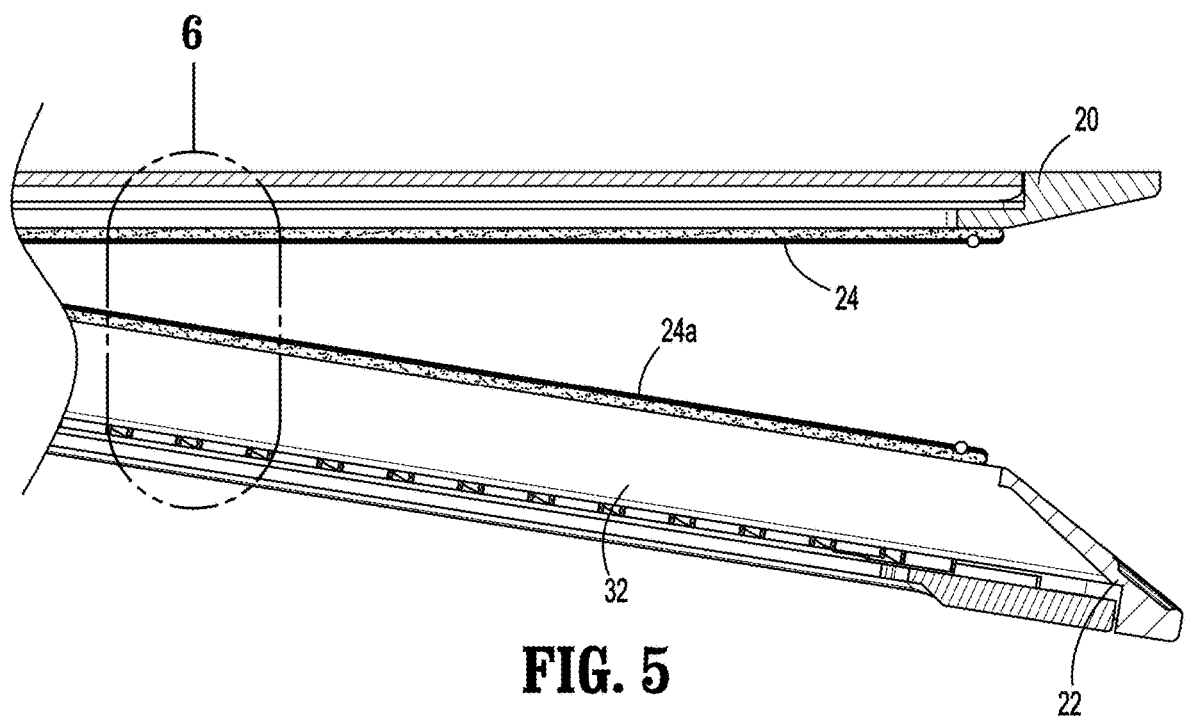
FIG. 5 is a cross-sectional view taken along section line 5-5 of FIG. 2, showing the configuration of the surgical buttresses of the present disclosure attached to the anvil assembly and the cartridge assembly, prior to firing of the surgical stapling apparatus of FIG. 1.

As illustrated in FIGS. 3-5, the staple clinching anvil jaw member 20 has been loaded with a surgical buttress 24, and the staple cartridge jaw member 22, including the staple cartridge 32, has been loaded with a surgical buttress 24a.

Although not depicted in the Figures, in some aspects a surgical stapler 10 of the present disclosure may have the surgical buttress 24 on the staple clinching anvil jaw member 20, the surgical buttress 24a on the staple cartridge jaw member 22, but not both.

Figure 6:
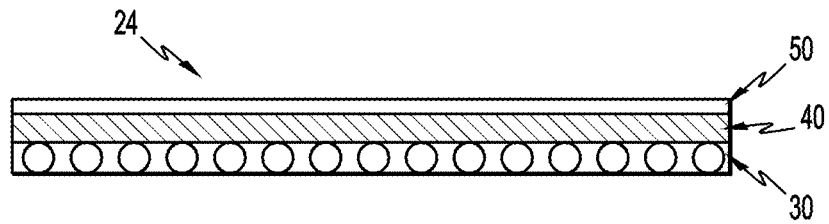
FIG. 6 is a side view of a surgical buttress of the present disclosure.
Figure 8:
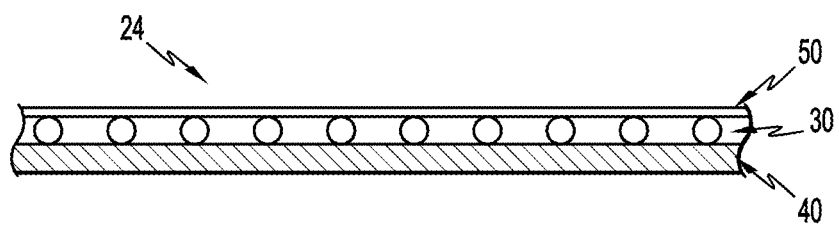
FIG. 8 is a side view of an alternate surgical buttress of the present disclosure.

With general reference to FIGS. 6 and 8, the surgical buttress 24 of the present disclosure may include multiple layers. The surgical buttress 24, for example, may include a substrate 30, a porous and/or swellable layer 40 and a non-permeable layer 50.

Any porous and/or swellable portion of a surgical buttress of the present disclosure, including the substrate 30 and/or the porous and/or swellable layer 40, may have openings or pores over at least a part of a surface thereof. Suitable porous and/or swellable materials for forming these layers include, but are not limited to, fibrous structures (e.g., knitted structures, woven structures, non-woven structures, etc.) and/or open cell foams.

Porous and/or swellable portions of the surgical buttress of the present disclosure may include fibrous materials, formed using any suitable method including, but not limited to, knitting, weaving, non-woven techniques (including melt blowing), wet-spinning, electro-spinning, extrusion, co-extrusion, and the like. Examples of a porous surgical buttress include those possessing a three dimensional structure, such as the textiles described in U.S. Pat. Nos. 7,021,086 and 6,443,964, the entire disclosures of each of which are incorporated by reference herein.

The porosity of the porous and/or swellable layer 40 and/or the substrate 30 may allow for the infiltration of biological fluids, molecules, including proteins, small molecules, RNA, etc., and/or cellular components which, in turn, may accelerate healing and/or the release kinetics of any therapeutic agent from the surgical buttress 24 of the present disclosure.

In aspects, materials used to form the layers of the surgical buttress may be biodegradable, so that the surgical buttress does not have to be retrieved from the body. The term "biodegradable" as used herein is defined to include both bioabsorbable and bioresorbable materials. By biodegradable, it is meant that the surgical buttress decomposes or loses structural integrity under body conditions (e.g., enzymatic degradation or hydrolysis), or is broken down (physically or chemically) under physiologic conditions in the body such that the degradation products are excretable or absorbable by the body.

Non-limiting examples of materials which may be biodegradable or non-degradable used in forming the various layers of the surgical buttress of the present disclosure include, but are not limited to, polyethylene glycol, poly (alkylene oxide) including poly(ethylene oxide) and poly (propylene oxide), poly(lactic acid), poly(glycolic acid), poly(alkylene carbonate) including poly(trimethylene carbonate), poly(dioxanone), poly(hydroxybutyrate), poly (phosphazine), poly(ethylene terephthalate), polyacrylamides, polyacrylate, polymethacrylate, poly (hydroxyethylmethylacrylate), poly(vinylpyrrolidone), poly (vinyl alcohols), polyacrylic acid, polyacetate, polycaprolactone, polypropylene, aliphatic polyesters, poly (glycerol ester) including poly(glycerol sebacate), poly (amino acids), copoly(ether-esters), polyalkylene oxalates, polyamides, poly(iminocarbonates), polyalkylene oxalates, polyoxaesters, polyorthoesters, polyurethane, poly(2-oxazoline), polymers with phosphoryl choline, sulfobetaine (SB), or carboxybetaine (CB) functional groups, and copolymers, block copolymers, homopolymers, blends and combinations thereof. The polymers may be in non-crosslinked or cross-linked form.

One embodiment of swellable materials is crosslinked poly(ethylene glycol) (PEG). PEG can be crosslinked by various crosslinking methods such as photochemical, free radical, click chemistry, NHS chemistry, addition chemistry such as Michael addition chemistry, thiol chemistry, Diels-Alder chemistry, condensation chemistry, genipin chemistry, urethane chemistry or supramolecular methods through hydrogen bonding or ionic or guest-host interactions. One embodiment of the crosslinking is by the NHS chemistry as illustrated in Example 1. The PEG before crosslinking can be linear with a molecular weight range of about 500 to 100,000 Dalton, or multi-arm with functionality of 3 to 10 and a molecular weight about 500 to 100,000 Dalton. Another embodiment is the crosslinked PEG degradable by introducing chemical bonds in the chain, which can break under physiological conditions such as hydrolysis. The degradation time can be tuned from 1 day to 1 year by changing the crosslinking density or the rate of hydrolysis of the ester bond for example. The swelling ratio can also be tuned from 1 to about 50 by changing the stoichiometric ratio, crosslinking density, the molecular weight between crosslinking points. The swelling ratio is defined as weight gain under physiological conditions vs the initial dry weight of the layer.

In aspects, natural biological polymers may be used in forming the various layers of the surgical buttress of the present disclosure. Suitable natural biological polymers include, but are not limited to, collagen, alginate, gelatin, hyaluronic acid, dextran, fibrin, fibrinogen, elastin, keratin, albumin, cellulose, oxidized cellulose, hydroxyethyl cellulose, hydroxypropyl cellulose, carboxyethyl cellulose, carboxymethyl cellulose, chitin, chitosan, and combinations thereof. In addition, natural biological polymers may be combined with any of the other polymeric materials described herein to produce a surgical buttress of the present disclosure.

The swellable layer optionally contains 0.05% to 7.5% antioxidants such as BHT to help with the stabilization during processing such as ETO and storage up to three years.

The swellable layer optionally contains 0.5% to 20% additives to improve the lubricity and the toughness of the material in the hydrated state. Examples of such additives include glycerol, low molecular weight PEG with molecular weight of 100 to 300.

The swellable and or porous layer may be formed by various crosslinking methods such as photochemical, free radical, click chemistry NHS chemistry, addition chemistry such as Michael addition chemistry, thiol chemistry, Diels-Alder chemistry, condensation chemistry, genipin chemistry, urethane chemistry or supramolecular methods through hydrogen bonding or ionic or guest-host interactions. The chemistry can be carried out in bulky or solution. The solvent can be organic such as methanol, ethanol or propanol. The preferred solvent is water or partially water. The working time prior to the gelation is between 5 minutes to 60 minutes. The stochiometric ratio of the reactants varies from 0.4 to 2.5. The concentration of the reactants varies from 1% to 100%. In the case of the aqueous reaction, the pH of the solutions varies from 5 to 10. The pH is controlled by a buffer such as phosphate buffer with concentration from 0.01 to 0.5M.

The porous structure of the swellable layer can be formed by various methods such as lyophilization process, salt out, selective leaching, electrospinning, etc.

The application of the layer to buttress can use a molding method in which the layer is formed in a tray and the buttress is positioned at the bottom or the top of the mold. The mold is made of metal and coated with non-sticking material such as PTFE. It can also be made of plastic material such as non-sticking PTFE or polyethylene etc. to facilitate the release of the swellable layer from the mold. The other application methods include spraying coating, slot die coating, electrospinning, hot pressing, etc.

In some aspects, the substrate 30 may be a non-woven substrate. In aspects, substrates include those formed of a biodegradable, porous matrix layer formed of a suitable material, for example a degradable polymer such as poly (lactic acid), poly(glycolic acid), poly(alkylene carbonate) including poly(trimethylene carbonate), polycaprolactone, poly(dioxanone), poly(hydroxybutyrate), poly(phosphazine). aliphatic polyesters, poly(glycerol ester) including poly (glycerol sebacate), poly(amino acids), copoly(ether-esters), polyalkylene oxalates, polyamides, poly(iminocarbonates), polyalkylene oxalates, polyoxaesters, polyorthoesters, and/or polyurethanes. The porous and/or swellable layer 40 may be formed of degradable polymers, polyethylene glycol, poly(alkylene oxide) including as poly(ethylene oxide) and poly(propylene oxide), alginate, collagen, gelatin, chitosan, dextran, hyaluronic acid, or a combination of these materials. In some aspects, the porous and/or swellable layer 40 may be a swellable material such as a hydrogel. The non-permeable layer 50 may be formed of degradable polymers, alginate, collagen, gelatin, chitosan, dextran, hyaluronic acid, thrombin, or a combination of these materials.

In aspects, the same material may be used to form both the porous and/or swellable layer and the non-permeable layer. This may be possible following methods within the purview of those skilled in the art, for example, cross-linking or physically pressing and compacting what would be a porous and/or swellable material to form a non-permeable material. The layer may be formed by various crosslinking methods such as photochemical, free radical, click chemistry NHS chemistry, addition chemistry such as Michael addition chemistry, thiol chemistry, Diels-Alder chemistry, condensation chemistry, genipin chemistry, urethane chemistry or supramolecular methods through hydrogen bonding or ionic or guest-host interactions. The chemistry can be carried out in bulky or solution. The solvent can be organic such as methanol, ethanol or propanol. The preferred solvent is water or partially water. The working time prior to the gelation is between 0.5 min to the 60 min. The stochiometric ratio of the reactants varies from 0.4 to 2.5. The concentration of the reactants varies from 1% to 100%. In the case of the aqueous reaction, the pH of the solutions varies from 5 to 10. The pH is controlled by a buffer such as phosphate buffer with concentration from 0.01 to 0.5M.

In aspects, the surgical buttress 24 may have a construction as depicted in FIG. 6, including the substrate 30, with the porous and/or swellable layer 40 formed over the substrate 30, and the non-permeable layer 50 formed over the porous and/or swellable layer 40. In use, the substrate 30 will be adjacent to the tissue.

Figure 7:
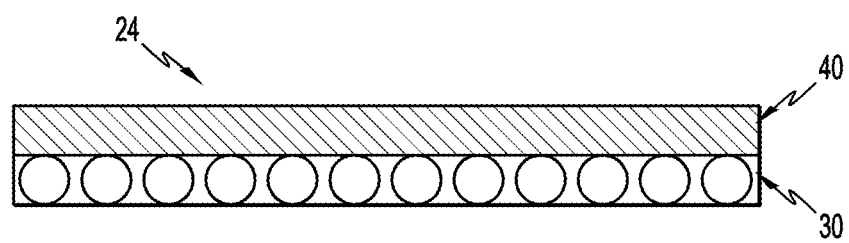
FIG. 7 is a side view of an alternate surgical buttress of the present disclosure.

In some aspects the surgical buttress may have a construction as depicted in FIG. 7, including the substrate 30, with the porous and/or swellable layer 40 formed over the substrate 30. In use, the substrate 30 will be adjacent to the tissue. The porous and/or swellable layer may on one side of the buttress or both sides. If the layer is on only one side of the buttress, it may be in contact with the tissue or away from the tissue.

In other aspects, the surgical buttress 24 may have a construction as depicted in FIG. 8, including the porous and/or swellable layer 40, the substrate 30 formed over the porous and/or swellable layer 40, and the non-permeable layer 50 formed over the substrate 30. In use, the porous and/or swellable layer 40 will be adjacent to the tissue.

Figure 9:
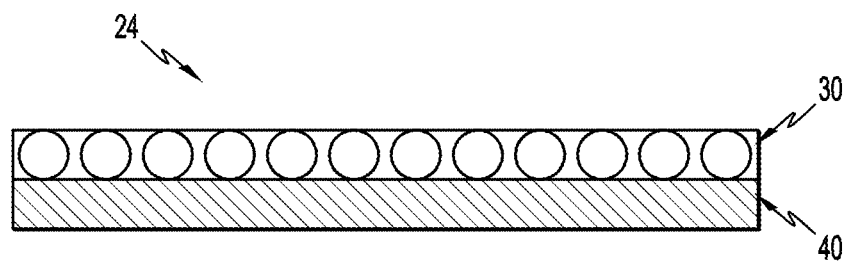
FIG. 9 is a side view of an alternate surgical buttress of the present disclosure.

In some aspects the surgical buttress may have a construction as depicted in FIG. 9, including the porous and/or swellable layer 40, with the substrate 30 formed over the porous and/or swellable layer 40. In use, the porous and/or swellable layer 40 will be adjacent to the tissue.

Figure 10:
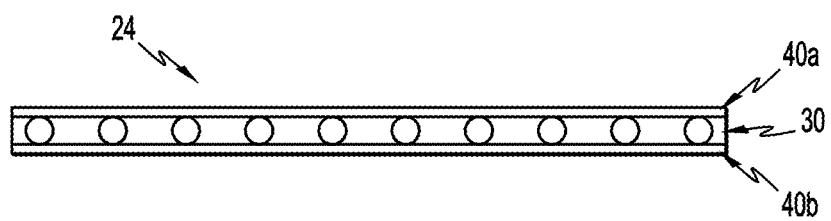
FIG. 10 is a side view of an alternate surgical buttress of the present disclosure.

In yet other aspects, the surgical buttress 24 may have a construction as depicted in FIG. 10, including the substrate 30 between two porous and/or swellable layers, 40a, 40b.

In aspects, the porous and/or swellable layer may penetrate into the pores of the substrate layer. In other aspects, the porous and/or swellable layer does not penetrate into the pores of the substrate layer.

While many of the depictions of the surgical buttress 24 show contiguous layers, it is to be understood that, in some embodiments, the layers may not be contiguous, i.e., the non-permeable layer 50 may extend beyond the borders of the substrate 30, the porous and/or swellable layer 40, or both. Similarly, the porous and/or swellable layer 40 may extend beyond the borders of the substrate 30. Although not depicted, layers of the surgical buttress 24 may also be non-contiguous, e.g., applied as a pattern to another layer. Any combination of the above may also be utilized. In yet other aspects (not shown), the porous and/or swellable layer may also be applied as a pattern on the substrate.

The substrate used to form the surgical buttress may have pores in an amount from about 65% to about 90% of the volume of the substrate, in aspects from about 70% to about 85% of the volume of the substrate.

Substrates used to form surgical buttresses of the present disclosure may have a thickness from about 0.05 mm to about 0.5 mm, in embodiments from about 0.1 mm to about 0.2 mm.

In use, the porous and/or swellable layer 40 may swell when introduced to fluids and/or staple line exudate, but will be restricted by the staples, exerting additional compression on the staple line. Swelling of the porous and/or swellable layer 40 may increase compression exerted on the staple line by the substrate. Swelling of the porous and/or swellable layer 40 may also fill gaps which may exist between the buttress 24 and staples, the buttress 24 and the tissue, and/or the staples and the tissue.

The swelling ratio of the porous and/or swellable layer may vary from 1 to 50. The swelling ratio is defined as weight gain under physiological conditions vs. the initial dry weight of the layer. The pore size may vary from 0.5 microns to 250 microns. The porous and/or swellable layer 40 used to form the surgical buttress may have pores in an amount from about 65% to about 99% of the volume of the porous layer, in aspects from about 70% to about 95% of the volume of the porous layer.

Porous and/or swellable layers used to form surgical buttresses of the present disclosure may have a non-compressed thickness from about 100 μm to about 2000 μm, in aspects from about 200 μm to about 1800 μm.

The non-permeable layer 50 acts as a physical barrier to leaks at the staple line and/or additional bleeding. The non-permeable layer 50 may also adsorb certain endogenous biological materials, including red blood cells, white blood cells, platelets, and the like, and thus aid in clot formation and/or wound healing.

Non-permeable layers used to form surgical buttresses of the present disclosure may have a thickness from about 5 μm to about 50 μm, in aspects from about 10 μm to about 30 μm.

Regardless of construction, in use the surgical buttress 24 will be compressible and will enable stapling through the surgical buttress and underlying tissue, without impeding function of the surgical stapler.

While the above description is directed to rectangular surgical buttresses, it is to be appreciated that any suitable configuration for a surgical buttress may be utilized in accordance with the present disclosure. For example, surgical buttresses having an elongate rectangular body with head and tail portions at the ends of the surgical buttress may be utilized. Any other suitable shape may be utilized, including circular or any other shape suitable use for surgical buttresses. For example, additional suitable surgical buttresses include those disclosed in U.S. Pat. Nos. 10,682,140, 8,157,151, 8,561,873 and 9,693,772, the entire disclosures of each of which are incorporated by reference herein.

Therapeutic agents may be added to a surgical buttress of the present disclosure for delivery to a patient. Suitable therapeutic agents include, but are not limited to, drugs, small molecules, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), ellagic acid, tranexamic acid, hormones and hormone analogs (e.g., growth hormone, luteinizing hormone releasing factor), vaccines (e.g., tumoral, bacterial and viral antigens), somatostatin, antigens, blood coagulation factors, growth factors (e.g., nerve growth factor, insulin-like growth factor), bone morphogenic proteins, TGF-B, protein inhibitors, protein antagonists, protein agonists, nucleic acids, such as antisense molecules, DNA, RNA, RNAi, oligonucleotides, polynucleotides, cells, viruses, anti-inflammatory agents, anti-bacterial agents, antimicrobial agents, antifungal agents, and ribozymes. In aspects, the therapeutic agent applied to a surgical buttress of the present disclosure may include an anti-tumor agent and/or tumor suppressor, referred to, in aspects, as a "chemotherapeutic agent" and/or an "antineoplastic agent." Suitable chemotherapeutic agents include, for example, paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine (BCNU), methyl-CCNU, cisplatin, etoposide, camptothecin and derivatives thereof, phenesterine, vinblastine, vincristine, goserelin, leuprolide, interferon alfa, retinoic acid (ATRA), nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, atezolizumab, canakinumab, combinations thereof, and the like. Other suitable therapeutic agents include immunotherapeutics, including pembrolizumab, nivolumab, atezolizumab, durvalumab, cemiplimab, and/or Osimertinib, cell targeting therapies, including iplimunmab, combinations thereof, and the like.

In aspects, paclitaxel and/or paclitaxel derivatives may be used as the therapeutic agent. Paclitaxel may have various forms, referred to herein as "polymorphs," including amorphous paclitaxel, crystalline paclitaxel, sometimes referred to as crystalline paclitaxel dihydrate, and/or anhydrous paclitaxel, or mixtures thereof.

Any therapeutic agent may be added to any layer of the surgical buttress 24, including the substrate 30, the porous and/or swellable layer 40, the non-permeable layer 50, or any combination thereof. For example, the therapeutic agent may be combined with the materials used to form the various layers, so that it is incorporated within the material forming the layer(s), or for non-woven or porous and/or swellable materials, the therapeutic agent may be present within the pores of the non-woven or porous and/or swellable material.

In aspects, as noted above, a surgical buttress of the present disclosure is provided to reinforce and seal the lines of staples applied to tissue by a surgical stapling apparatus. Upon application to a site of bleeding tissue, the surgical buttress may affect hemostasis of said tissue. As used herein, the term "hemostasis" means the arrest of bleeding.

In addition to providing hemostasis at the site of application of the surgical buttress, the surgical buttresses of the present disclosure may also provide for treatment of tissue with a therapeutic agent at both the site of implantation and elsewhere in the body.

In accordance with the present disclosure, buttresses having desirable characteristics may be designed and/or constructed considering at least some of the following factors:

Buttress and properties of the various layers, including the porous and/or swellable layer and the non-permeable layer, result in increasing leak pressures which may also improve staple line hemostasis.

Certain materials for the substrate, for example polyglycolic acid, which is stiffer, may provide more mechanical compression in the staple line than other materials; buttress stiffness may best be altered by tuning density and thickness of the substrate.

Increasing density and/or thickness of the substrate beyond a certain point may adversely impact staple formation, firing, and retraction forces, and staple line abrasiveness.

Porous and/or swellable layers that swell with fluid absorption may enable greater final buttress thicknesses.

Porous and/or swellable layers that produce expansile forces during swelling may tend to increase buttress compression on tissue and around staple hole defects; larger expansile forces may be desirable to improve resistance to leaks and bleeding both intra-operatively and post-operatively.

Elastic properties of the buttress and/or the porous and/or swellable layer allow expansion lateral to the buttress edges, enabling coverage of cut edge and tissue prone to tearing adjacent the staple line.

Increasing expansile forces beyond a certain point may adversely impact staple formation and firing and/or retraction forces.

Degree of swelling and expansile forces can be readily tuned and controlled using some synthetic materials, for example polyethylene glycol, when compared with natural materials such as collagen and alginate.

Greater swelling may increase endogenous growth factor absorption, leading to improved healing and fewer post-operative leaks.

Blood clots in the layers of the buttress (either passively or with the aid of active clotting agents)

Platelets in clot supply growth factors to healing staple line.

Buttress mechanically protects clot from delaminating from staple line.

Greater clot adhesivity may reduce likelihood of leaks and bleeding and may enable a larger reservoir of growth factors for staple line healing.

New tissue grows into buttress over time.

Buttress may protect staple line from the formation of adhesions post-operatively Example 1

Figure 11:
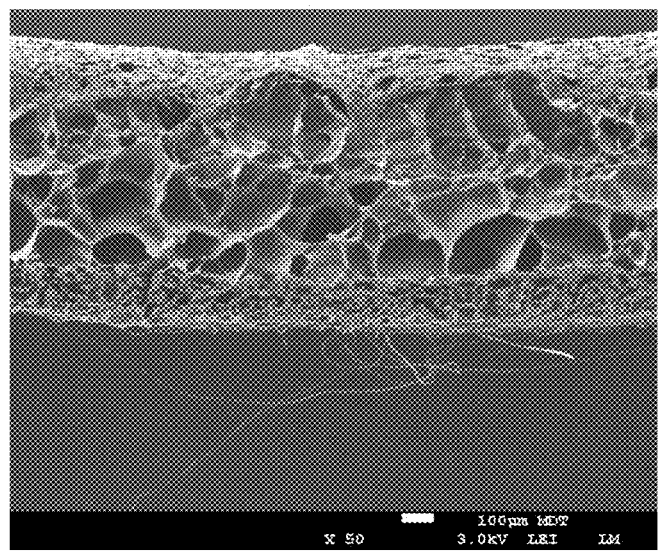
FIG. 11 is a scanning electron microscope image of a surgical buttress produced in accordance with Example 1 of the present disclosure.

Preparation the buttress described herein. 4.5 mL of deionized water (pH ca 6.7) was added to a 20 mL glass vial with 0.3 grams of poly(ethylene glycol) diamine having a molecular weight 10,000 Dalton and the mixture was vortexed to make a homogeneous solution. A second solution of 0.15 grams of 4-arm poly(ethyelene glycol) succinimidyl glutarate ((4-arm PEG SG)) with a molecular weight of 10,000 Dalton in 1.5 mL deionized water was made similarly. The two solutions were mixed and vortexed to make a homogeneous solution to start the crosslinking reaction by NHS chemistry. A stainless 10× 4 cm tray with a depth of 1 mm and coated with PTFE was filled with the solution prior to the gelation in about 10 minutes. Immediately a poly(glycolic acid) non-woven buttress sheet with 0.15 mm thickness was laid on the top of the tray. The tray sat on a flat surface for 2 hours before being put in a −80° C. freezer for 1 hour. The tray was transferred to a lyophilizer. The lyophilization was at −20° C. in an oven under high vacuum for 24 hours and the remaining residual water was removed to a room temperature oven for another 24 hours under high vacuum. The coated buttress was removed by peeling of the tray. The cross-section of the coated buttress was imaged by scanning electron microscopy (SEM), which showed good integration of the porous crosslinked PEG layer to the buttress. The SEM image of the coated buttress is provided as FIG. 11.

Example 2

In a primary, acute, in vivo preclinical setting, the buttress described herein, when used with a surgical stapler, demonstrated significantly fewer staple line bleeding events, and significantly higher stapler line leak pressure, when compared to other commercially available buttress materials:

Comparative Example A: Tri-Staple™ 2.0 Reinforced Reload (Medtronic)

Comparative Example B: GORE® SEAMGUARD® (GORE)

Comparative Example C: ECHELON ENDOPATH™ Staple line Reinforcement (Ethicon)

Buttressed staple lines were placed longitudinally along the anti-mesenteric border of canine small bowel maintaining at least 50% patency of the lumen. Upon release of the tissue from the surgical stapler, the occurrence of a bleeding event was recorded (defined as any visible oozing of blood from the staple line after initial blotting), and the bleeding severity was assessed and recorded based on the following Likert Scale:

TABLE 1

| Hemostasis rating scale[1] | |
| --- | --- |
| Score | Description |
| 0 | No bleeding at the tissue site after initial blotting of staple line |
| 1 | Blood oozing at the tissue site; stops prior to 1 min; no intervention needed |
| 2 | Blood oozing, still progressive after 1 min through 3 min; no intervention needed |
| 3 | Blood oozing at tissue site after 3 min, mild intervention needed (i.e. cautery) |
| 4 | Significant bleeding requiring intervention such as extensive coagulation of ligation with clips |

[1]Siegel JM, et al. Journal of Advances in Medical and Pharmaceutical Sciences, 1(1): 30-39, 2014.

Leak testing was performed for each buttressed staple line using a Z-axis system (Isaac HD Muti-Function Leak Tester). The section of bowel that contained the staple line was clamped off for testing, and the staple line was wetted with saline. The Z-axis needle was inserted into the pouch longitudinally and pressure was increased incrementally until a leak (defined as the appearance of air bubbles at the staple or cut line) was observed and that pressure was recorded.

Results:

Bleeding

The buttress described herein resulted in no staple line bleeding for all samples tested, and significantly fewer bleeding events than Comparative Example C (Tables 3 and 4).

TABLE 2

| Bleeding Severity (based on Scale) | | | |
| --- | --- | --- | --- |
| Group | N | Median | Mean ± Standard Deviation |
| Buttress described herein | 7 | 0 | 0.0 ± 0.0 |
| A (Medtronic) | 7 | 0 | 0.7 ± 1.0 |
| B (GORE) | 7 | 0 | 0.0 ± 0.0 |
| C (Ethicon) | 6 | 2 | 1.7 ± 0.8 |

TABLE 3

Bleeding Events

| Group | % | Events | P-Value* |
|---|---|---|---|
| Buttress described herein | 0.0 | 0/7 | — |
| A (Medtronic) | 42.9 | 4/7 | 0.192 |
| B (GORE) | 0.0 | 0/7 | 1.000 |
| C (Ethicon) | 83.3 | 5/6 | 0.005 |

*P-value based on comparison of the buttress described herein and each other group individually using a two-proportion, Fisher exact test. A p-value < 0.050 is considered statistically significant.

Leak Testing

The buttress described herein resulted in significantly higher staple line leak pressure as compared to all other Comparative Examples, as determined by One-way ANOVA with Tukey Pairwise Comparisons (Tables 4 and 5). A p-value<0.050 is considered statistically significant. No other differences between Examples were observed.

TABLE 4

Staple Line Leak Pressure Summary

| Group | N | Mean ± Standard Deviation (mm Hg) |
|---|---|---|
| Buttress described herein | 7 | 173.1 ± 35.2 |
| A (Medtronic) | 6 | 133.7 ± 30.5 |
| B (GORE) | 7 | 106.2 ± 16.2 |
| C (Ethicon) | 6 | 94.1 ± 18.7 |

TABLE 5

Tukey Simultaneous Tests for Differences of Means

| Difference of Levels | Difference of Means | SE of Difference | 95% CI | T-Value | Adjusted P-Value |
|---|---|---|---|---|---|
| Buttress described herein - A | 40.4 | 14.5 | (0.2, 80.6) | 2.79 | 0.048 |
| B - A | −27.5 | 13.9 | (−66.1, 11.1) | −1.98 | 0.227 |
| C - A | −39.6 | 14.5 | (−79.8, 0.6) | −2.74 | 0.054 |
| B - buttress described herein | −67.9 | 14.5 | (−108.1, −27.7) | −4.69 | 0.001 |
| C - buttress described herein | −80.0 | 15.0 | (−121.8, −38.3) | −5.33 | 0.000 |
| C - B | −12.1 | 14.5 | (−52.3, 28.1) | −0.84 | 0.836 |

Individual confidence level = 98.91%

Chronic Preclinical Model

Furthermore, using the canine preclinical model and leak test method described previously, the buttress described herein resulted in significantly higher staple line leak pressure in a chronic assessment when compared to Comparative Example A, as determined by One-way ANOVA with Tukey Pairwise Comparisons. Staple line leak pressures were determined post-mortem on post-operative day 3 (Tables 6 and 7).

TABLE 6

Post-Mortem Staple Line Leak Pressure Summary, Post-Operative Day 3

| Group | N | Mean ± Standard Deviation (mm Hg) |
|---|---|---|
| Non-buttressed | 6 | 81.1 ± 19.9 |
| A (Medtronic) | 6 | 71.9 ± 14.2 |
| Buttress described herein | 6 | 110.1 ± 35.5 |

TABLE 7

Tukey Simultaneous Tests for Differences of Means

| Difference of Levels | Difference of Means | SE of Difference | 95% CI | T-Value | Adjusted P-Value |
|---|---|---|---|---|---|
| A - Non-buttressed | −9.3 | 14.4 | (−46.6, 28.0) | −0.64 | 0.798 |
| Buttress described herein - Non-buttressed | 28.9 | 14.4 | (−8.4, 66.2) | 2.01 | 0.143 |
| Buttress described herein - A | 38.2 | 14.4 | (0.9, 75.5) | 2.66 | 0.045 |

Individual confidence level = 97.97%

It will be understood that various modifications may be made to the aspects disclosed herein. Therefore, the above description should not be construed as limiting, but merely as an exemplification of preferred aspects. Those skilled in the art will envision other modifications within the scope and spirit of the present disclosure. Such modifications and variations are intended to come within the scope of the following claims.

What is claimed is:

1. A surgical stapling device, comprising:
    an end effector including an anvil jaw member and a staple cartridge jaw member pivotally coupled to one another, the anvil jaw member and the staple cartridge jaw member being relatively movable such that the end effector is movable between an open position and a clamped position; and
    a surgical buttress attached to the anvil jaw member, the staple cartridge jaw member, or both, the surgical buttress including a substrate having a thickness from 0.05 mm to 0.5 mm and a porous layer having a non-compressed thickness from 100 µm to 2000 µm.

2. The surgical stapling device of claim 1, wherein, in use, the substrate of the surgical buttress is adjacent tissue, and the porous layer of the surgical buttress is adjacent the substrate of the surgical buttress.

3. The surgical stapling device of claim 1, wherein, in use, the porous layer of the surgical buttress is adjacent tissue, and the substrate of the surgical buttress is adjacent the porous layer of the surgical buttress.

4. The surgical stapling device of claim 1, wherein the porous layer includes a first porous layer and a second porous layer and, in use, the first porous layer of the surgical buttress is adjacent tissue, the substrate of the surgical buttress is adjacent the first porous layer of the surgical buttress, and the second porous layer of the surgical buttress is adjacent the substrate of the surgical buttress.

5. The surgical stapling device of claim 1, wherein the surgical buttress further comprises a non-permeable layer.

6. The surgical stapling device of claim 5, wherein, in use, the substrate of the surgical buttress is adjacent tissue, the porous layer of the surgical buttress is adjacent the substrate of the surgical buttress, and the non-permeable layer of the surgical buttress is adjacent the porous layer of the surgical buttress.

7. The surgical stapling device of claim 5, wherein, in use, the porous layer of the surgical buttress is adjacent tissue, the substrate of the surgical buttress is adjacent the porous layer of the surgical buttress, and the non-permeable layer of the surgical buttress is adjacent the substrate of the surgical buttress.

8. The surgical stapling device of claim 5, wherein the non-permeable layer of the surgical buttress has a thickness from 5 μm to 50 μm.

9. The surgical stapling device of claim 1, wherein the substrate of the surgical buttress has pores in an amount from 65% to 85% of the volume of the substrate.

10. The surgical stapling device of claim 1, wherein the porous layer of the surgical buttress has pores in an amount from 65% to 99% of the volume of the porous layer.

11. A method for treating tissue comprising stapling tissue with the surgical stapling device of claim 1.

12. A surgical stapling device, comprising:
an end effector including an anvil jaw member and a staple cartridge jaw member pivotally coupled to one another, the anvil jaw member and the staple cartridge jaw member being relatively movable such that the end effector is movable between an open position and a clamped position; and
a surgical buttress attached to the anvil jaw member, the staple cartridge jaw member, or both, the surgical buttress including a substrate having a thickness from 0.05 mm to 0.5 mm, a porous layer having a non-compressed thickness from 100 μm to 2000 μm, and a non-permeable layer having a thickness from about 5 μm to about 50 μm.

13. The surgical stapling device of claim 12, wherein, in use, the substrate of the surgical buttress is adjacent tissue, the porous layer of the surgical buttress is adjacent the substrate of the surgical buttress, and the non-permeable layer of the surgical buttress is adjacent the porous layer of the surgical buttress.

14. The surgical stapling device of claim 12, wherein, in use, the porous layer of the surgical buttress is adjacent tissue, the substrate of the surgical buttress is adjacent the porous layer of the surgical buttress, and the non-permeable layer of the surgical buttress is adjacent the substrate of the surgical buttress.

15. The surgical stapling device of claim 12, wherein the substrate of the surgical buttress has pores in an amount from 65% to 85% of the volume of the substrate.

16. The surgical stapling device of claim 12, wherein the porous layer of the surgical buttress has pores in an amount from 65% to 99% of the volume of the porous layer.

17. A method for treating tissue comprising stapling tissue with the surgical stapling device of claim 12.

18. A surgical buttress comprising:
a substrate having pores in an amount from 65% to 85% of the volume of the substrate, and a thickness from 0.05 mm to 0.5 mm;
a porous layer having pores in an amount from 65% to 99% of the volume of the porous layer, and a non-compressed thickness from 100 μm to 2000 μm; and
a non-permeable layer having a thickness from 5 μm to 50 μm.

19. The surgical buttress of claim 18, wherein, in use, the substrate of the surgical buttress is adjacent tissue, the porous layer of the substrate is adjacent the substrate of the surgical buttress, and the non-permeable layer of the surgical buttress is adjacent the porous layer of the surgical buttress.

* * * * *